United States Patent
Lazo et al.

(10) Patent No.: US 10,308,663 B2
(45) Date of Patent: Jun. 4, 2019

(54) INHIBITORS OF PTP4A3 FOR THE TREATMENT OF CANCER

(71) Applicants: John S. Lazo, Charlottesville, VA (US); Elizabeth R. Sharlow, Butler, PA (US); Kelley E. McQueeney, Charlottesville, VA (US); Peter Wipf, Pittsburgh, PA (US); Joseph M. Salamoun, Roanoke, VA (US)

(72) Inventors: John S. Lazo, Charlottesville, VA (US); Elizabeth R. Sharlow, Butler, PA (US); Kelley E. McQueeney, Charlottesville, VA (US); Peter Wipf, Pittsburgh, PA (US); Joseph M. Salamoun, Roanoke, VA (US)

(73) Assignees: University of Virginia Patent Foundation, Charlottesville, VA (US); University of Pittsburgh —Of the Commonwealth System of Higher Education, Pittsburgh, PA (US)

( * ) Notice: Subject to any disclaimer, the term of this patent is extended or adjusted under 35 U.S.C. 154(b) by 27 days.

(21) Appl. No.: 15/737,062

(22) PCT Filed: Jun. 16, 2016

(86) PCT No.: PCT/US2016/037895
§ 371 (c)(1),
(2) Date: Dec. 15, 2017

(87) PCT Pub. No.: WO2016/205534
PCT Pub. Date: Dec. 22, 2016

(65) Prior Publication Data
US 2018/0170946 A1 Jun. 21, 2018

Related U.S. Application Data

(60) Provisional application No. 62/332,559, filed on May 6, 2016, provisional application No. 62/180,299, filed on Jun. 16, 2015.

(51) Int. Cl.
C07D 495/04 (2006.01)
A61K 31/4365 (2006.01)
A61P 35/00 (2006.01)

(52) U.S. Cl.
CPC ........ *C07D 495/04* (2013.01); *A61K 31/4365* (2013.01); *A61P 35/00* (2018.01)

(58) Field of Classification Search
CPC .... C07D 495/04; A61P 35/00; A61K 31/4365
See application file for complete search history.

(56) References Cited

FOREIGN PATENT DOCUMENTS

WO   WO-2009135580 A1   11/2009
WO   WO-2016205534 A1   12/2016

OTHER PUBLICATIONS

"International Application Serial No. PCT/US2016/037895, International Search Report dated Aug. 19, 2016", 5 pgs.
"International Application Serial No. PCT/US2016/037895, Written Opinion dated Aug. 19, 2016", 5 pgs.
Daouti, S, et al., "A Selective Phosphatase of Regenerating Liver Phosphatase Inhibitor Suppresses Tumor Cell Anchorage-Independent Growth by a Novel Mechanism Involving p130Cas Cleavage", Cancer Research, vol. 68, No. 4, (Feb. 15, 2008), 1162-1169 pgs.
Garam, Min, et al., "Rhodanine-based PRL-3 inhibitors blocked the migration and invasion of metastatic cancer cells", Bioorganic & Medicinal Chemistry Letters, vol. 23, No. 13, (May 9, 2013), 3769-3774 pgs.
Salamoun, Joseph M, et al., "Photooxygenation of an aminothienopyridone yields a more potent PTP4A3 inhibitor", Organic & Biomolecular Chemistry vol. 14, No. 27, (Jun. 7, 2016), 6398-6402 pgs.
Sharlow, Elizabeth R, et al., "Investigational inhibitors of PTP4A3 phosphatase as antineoplastic agents", Expert Opinion on Investigational Drugs vol. 23, No. 5, (Mar. 13, 2014), 661-673 pgs.
"European Application Serial No. 16734519.8 Response filed Aug. 14, 2018 to Communication pursuant to Rules 161(1) and 162 EPC", 9 pgs.

*Primary Examiner* — John M Mauro
(74) *Attorney, Agent, or Firm* — Schwegman Lundberg & Woessner, P.A.

(57) ABSTRACT

The invention provides protein tyrosine phosphatase inhibitor compounds, Their pharmaceutical compositions, uses, and methods of use, such as in the treatment of various cancers, and process for making the compounds. Also disclosed is an improved synthesis of protein tyrosine phosphatase inhibitor and precursor compound thienopyridone (5).

12 Claims, 2 Drawing Sheets

INHIBITORS OF PTP4A3 FOR THE TREATMENT OF CANCER

RELATED APPLICATIONS

The present application is a U.S. National Stage Filing under 35 U.S.C. 371 from International Application No. PCT/US2016/037895, filed on Jun. 16, 2016, and published as WO 2016/205534, which claims the benefit of priority to U.S. Provisional Patent Applications No. 62/332,559 filed on May 6, 2016 and No. 62/180,299 filed on Jun. 16, 2015, which applications are incorporated as if fully set forth herein.

STATEMENT REGARDING FEDERALLY SPONSORED RESEARCH OR DEVELOPMENT

This invention was made with government support under Grant No. CA191944, awarded by The National Institutes of Health. The government has certain rights in the invention.

BACKGROUND

Phosphatases, as therapeutic targets, offer a largely underexplored opportunity for the discovery of novel drugs and expansion of the current state of the art in medicinal chemistry. In recent years, the protein tyrosine phosphatase 4A family (PTP4A1, PTP4A2, and PTP4A3) has garnered much interest and ample validation as an anticancer target. All three phosphatases are ~20 kD and possess a unique C-terminal prenylation motif important for association with the plasma membrane and early endosomes. There is no established substrate for any PTP4A family member.

Compared to other phosphatases, PTP4A3 has a higher rate of overexpression in many cancer cell lines, especially in colorectal cancer, potentially allowing for a more selective inhibition by drug molecules. Elevated levels of PTP4A3 mRNA were first observed in metastatic colorectal cancer and is associated with late stage metastatic disease. Other human cancers express high PTP4A3 levels including, but not restricted to tumors of the breast, ovary, cervix, lung, brain, prostate, liver, stomach, and stroma and to leukemias and lymphomas. Elevated PTP4A3 expression often correlates with increased tumor invasiveness and poor prognosis and ectopic PTP4A3 overexpression enhances tumor cell migration and invasion in vitro. PTP4A3 also has been proposed to have a role in the progression of cardiac hypertrophy by inhibiting intracellular calcium mobilization in response to angiotensin II.

There is a long felt need in the art for compositions and methods useful for inhibiting protein tyrosine phosphatases and for treating diseases and disorders. The present invention satisfies these needs.

SUMMARY OF THE INVENTION

The present application provides new methods and compounds for treating cancer, inhibiting tumor cell migration, and inhibiting tumor cell adhesion. In one aspect, the compounds are derivatives or analogs of thienopyridone (also referred to as JMS-631-050 herein).

Disclosed herein are new potent inhibitors of PTP4A3. In one aspect, the inhibitors are nanomolar inhibitors of the phosphatase activity of PTP4A3. In one aspect, the inhibitor is JMS-631-053D. In one aspect, the inhibitory compounds of the invention are useful for inhibiting tumor cell proliferation, invasion and metastasis. In one aspect, the compounds of the invention are useful for treating cancer.

It is disclosed herein that JMS-631-053D provides significant and potent growth inhibition of mouse colorectal and ovarian tumor cells, and severely hinders wound healing in a mouse colorectal tumor cell migration assay. Significantly, JMS-631-053D was highly potent in the target protein and cell assays and showed markedly decreased inhibition against twenty-two other phosphatases.

JMS-631-053

7-imino-2-phenylthieno[3,2-c]pyridine-4,6(5H,7H)-dione

JMS-361-050 (Also Referred to Thienopyridone).

The present application further provides compositions and methods for synthesizing compounds of the invention, for testing activity of the compounds, and for using the compounds as described herein.

For instance, in some embodiments, the invention provides a method for treating a subject suffering from cancer, comprising administering to the subject a therapeutically effective amount of a compound described herein, such as according to Formula III, or a pharmaceutically acceptable salt thereof.

In another embodiment, the invention provides a method for inhibiting a protein-tyrosine phosphatase in a cell, comprising contacting the cell with a compound as described herein, such as according to Formula III, or a pharmaceutically acceptable salt thereof.

Also provided in various embodiments are uses of the compounds. Thus, in one embodiment, the invention provides the use of a compound described herein in the manufacture of a medicament for treating cancer. Another embodiment provides the use of a compound in the manufacture of a medicament for inhibiting a protein tyrosine phosphatase in a cell. In various embodiments, the compound can be one according to Formula III or a pharmaceutically acceptable salt thereof.

The present invention provides compounds useful for inhibiting cell migration. The present invention provides compounds useful for inhibiting cell adhesion. In one aspect, the cells are tumor cells.

Further disclosed herein are cell lines. The present invention provides an isogenic Ptp4a3 null cell pair: MsTuWT and MsTuKO.

The present application provides pharmacological tools useful for making and testing compounds of the invention. The present application provides new active and inactive thienopyridone-based molecules and discloses their characteristics relative to known compounds.

The present application discloses that genetic or pharmacologic loss/inhibition of PTP4A3 inhibits cell migration. It is also disclosed herein that loss or inhibition of PTP4A3 inhibits cell adhesion. It is also disclosed herein that loss or inhibition of PTP4A3 inhibits spheroid formation.

Compounds of the invention such as JMS-631-053 are highly selective for inhibiting PTP4A3 relative to other phosphatases and is very potent in its ability to inhibit PTP4A3 activity.

The present application further discloses that cancer cells such as a cisplatin resistant human ovarian cancer cells are still susceptible to the compounds of the invention and that they are sensitive to growth inhibition by PTP4A3 inhibitors.

The present invention further provides inactive analogs and derivatives that are inactive against PTP4A3 and useful as tools for studying the role of this phosphatase.

The compounds of the invention active as inhibitors of PTP4A3 are also useful for treating cardiac hypertrophy.

Various aspects and embodiments of the invention are described in further detail below.

BRIEF DESCRIPTION OF THE DRAWINGS

FIG. 4A-F shows results of cell adhesion assays with thienopyridone (5). Images A and B: MsTuWT in poly-HEMA coated plates. Image C: MsTuWT in matrigel. Images D and E: MsTuKO in polyHEMA coated plates. Image F: MsTuKO in Matrigel. WT=PTP4A3 wild-type; KO=PTP4A3 knock-out.

DETAILED DESCRIPTION

Abbreviations and Acronyms

DiFMUP—6,8-difluoro-4-methylumbelliferyl phosphate
KO—null
PTP4A—protein tyrosine phosphatase 4A
WT—wildtype Definitions JMS-631-053D is also referred to as JMS-631-053 herein.

Thienopyridone is also referred to as JMS-631-050 herein.

In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder, which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter that when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material that can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity."

The term "inhibit," as used herein, refers to the ability of a compound of the invention to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

As used herein "injecting or applying" includes administration of a compound of the invention by any number of routes and means including, but not limited to, topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression, which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container that contains the identified compound invention or be shipped together with a container that contains the identified compound. Alternatively, the instructional material may be shipped separately from the container with the intention that the instructional material and the compound be used cooperatively by the recipient.

The term "modulate", as used herein, refers to changing the level of an activity, function, or process. The term "modulate" encompasses both inhibiting and stimulating an activity, function, or process.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "subject" of diagnosis or treatment is a mammal, including a human, as well as other organisms of interest.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound that is sufficient to provide a beneficial effect to the subject to which the compound is administered.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. Optionally substituted aryl includes aryl compounds having from zero to four substituents, and A substituted aryl includes aryl compounds having one or more substituents. The term ($C_5$-$C_8$ alkyl)aryl refers to any aryl group that is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and that consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and that consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom that affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

The term "pharmaceutically-acceptable salt" refers to salts that retain the biological effectiveness and properties of the compounds of the present invention and that are not biologically or otherwise undesirable. In many cases, the compounds of the present invention are capable of forming acid and/or base salts by virtue of the presence of amino and/or carboxyl groups or groups similar thereto. Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

EMBODIMENTS

As described herein, the compositions of the present invention comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

In various embodiments, the invention provides for compounds conforming to Formulae I, II, and III as shown below:

(I)

(II)

(III)

Based on the methods and compositions provided herein, one of ordinary skill in the art will appreciate that the present invention encompasses modification of the compounds described herein and methods to determine which modifications are useful for the activity disclosed herein. The present application provides generic formulas encompassing useful compounds of the invention. One of ordinary skill in the art, based on the disclosure herein, will be able to make and use compounds of the present invention, including those encompassed by, for example, Formula I, Formula II, and Formula III.

For example, in one embodiment, $R_1$, $R_2$, $R_3$, and $R_4$ are each independently, for example, H, N, C, hydrogen, —OH, —COOH, —OCNH$_2$, —OCH$_3$, halogen, —OC$_2$H$_5$, —SCH$_3$, —OCF$_3$, —CF$_3$N, —CH3, O, S, In another embodiment, $R_1$, $R_2$, $R_3$, and $R_4$ may be the same or different, and are independently —OH, —OC$_{1-4}$ alkyl, —OR$^a$, trifluoroC$_{1-4}$ alkoxy, —SC$_{1-4}$ alkyl, —S—R$^a$, —SO$_2$—C$_{1-4}$ alkyl, —SO$_2$—R$^a$, —SOC$_{1-4}$ alkyl, —SO—R$^a$, —SO$_2$—NH—R$^b$, —NR$^C$R$^d$, halo, —C$_{1-4}$ alkyl, —C$_{5-12}$ alkyl, —C$_{2-6}$ alkenyl, —C$_{2-6}$ alkynyl, —C$_{3-6}$ cycloalkyl, or phenyl, benzyl, or monocyclic heteroaryl optionally substituted with R$^b$, —C$_{3-6}$ cycloalkyl optionally containing O, S, N, or Hydrogen, —OC(O)—R$^b$, —OC(O)—R$^b$, —P(O)(O R$^b$)$_{1-2}$, —P(S)(O R$^b$)$_{1-2}$, —P(O)(NR$^C$R$^d$)$_{1-2}$, —P(S)(NR$^C$R$^d$)$_{1-2}$, —O(CH$_2$—CH$_2$—O)$_{1-4}$ CH$_3$, —CN, —COOH, —NO2, —C(O)—C$_{1-4}$ alkyl, or —C(O)—R$^b$, $R^a$ is —C$_{3-6}$ cycloalkyl, —C$_{2-6}$ alkenyl, —C$_{2-6}$ alkynyl, phenyl, benzyl, or monocyclic heteroaryl ring, wherein the phenyl, benzyl, or monocyclic heteroaryl ring is optionally substituted with R$^b$;

$R^b$ is independently H, halo, —OH, —COOH, —C$_{1-4}$ alkyl, C$_{5-12}$ alkyl, phenyl, benzyl, or monocyclic heteroaryl ring, wherein the phenyl, benzyl, or monocyclic heteroaryl ring is optionally substituted with $R^b$, —$C_{2-6}$ alkenyl, —$C_{2-6}$ alkynyl, trifluro$C_{1-4}$ alkoxy, —$OC_{1-4}$ alkyl, —O(CH$_2$—CH$_2$—O)$_{1-4}$ CH$_3$, —O-phenyl, —O-benzyl, —N$C_{1-4}$ alkyl, —N-phenyl, and —N-benzyl, —N-monocyclic heteroaryl ring optionally substituted with $R^b$;

$R^C$ and $R^d$ are each independently H, —$C_{1-4}$ alkyl, —$C_{1-4}$ alkyl, —C(O)—$C_{1-4}$ alkyl, —C(O)—$R^e$, —$C_{1-4}$ alkyl-$R^e$, —SO$_2$$R^a$, —SO$_2$—$C_{1-4}$ alkyl, phenyl, benzyl, or monocyclic heteroaryl ring, wherein the phenyl, benzyl, or monocyclic heteroaryl ring is optionally substituted with $R^b$, and optionally $R^C$ and $R^d$ can be taken together with the nitrogen to which they are attached to form an optionally substituted monocyclic heterocycloalkyl ring optionally containing one or more O, S, N.

The terms halo, alkyl, etc., are elaborated as follows:

The term halo represents chloro, fluoro, bromo or iodo and also perhaloalkyl groups, including, but not limited to —CF$_3$, —CF$_2$H, and CH$_2$CF$_3$.

Alkyl refers to straight or branched chain alkyl groups having from methyl, ethyl, n-propyl, isopropyl, butyl, isobutyl, tert-butyl and so on.

Cycloalkyl refers to saturated or partially saturated, monocyclic, polycyclic and spiro polycyclic carbocycle having 3-6 atoms per carbocycle. Illustrative examples of cycloalkyl groups as follows in the properly bonded moieties include:

The term heterocycloalkyl refers to monocyclic ring that is saturated or partially saturated and has 4-7 atoms selected from carbon atoms and up to two heteroatoms like nitrogen, sulfur, and oxygen monocyclic, polycyclic and spiro polycyclic carbocycle having 3-6 atoms per carbocycle. Illustrative examples in the form of properly bonded moieties include:

The term heteroaryl refers to monocyclic, fused bicyclic or polycyclic aromatic heterocycle consists of ring atoms selected from carbon atoms and up to four heteroatoms like nitrogen, sulfur, and oxygen. Illustrative examples of heterocyclic rings in the form of properly bonded moieties include:

The listed examples of cycloalkyl, heterocycloalkyl, heteroaryl above are not limited and that additional species within the scope of defined terms may also be considered.

In one embodiment, all tautomeric and isomeric forms and mixtures thereof are considered within the scope of the Formulae I-III and pharmaceutically acceptable salts, pharmaceutically active metabolites and prodrugs of Formulae I-III are encompassed within the present invention.

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

Processes for preparing compounds of any of the formulas of the invention or for preparing intermediates useful for preparing compounds of any of the formulas of the invention are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of formula I to the skin, are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. These ranges are not exclusive and include subranges and individual doses and unit doses as well. In one aspect, about 1, 5, 10, 12, 15, 17, 20, 25, 30, 25, 40, 45, 50, 55, 60, 65, 70, 75, 80, 85, 90, 95, or 100 mg/kg is administered. Multiple doses can be used and the timing can vary as to when to administer the drug, as well as the amount per administration. Doses can be administered daily, more than once per day, weekly, more than once per week, monthly, and more than once per month. In one aspect, the first dose is greater than subsequent doses.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound. This may be achieved, for example, by the intravenous injection of a 0.05 to 5% solution of the active ingredient.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Examples of other antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the invention can first be encapsulated into microcapsules, microspheres, microparticles, nanoparticles, liposomes, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression, which can be used to communicate the usefulness of the composition of the invention for its designated use. The instructional material of the kit of the invention may, for example, be affixed to a container that contains the composition or be shipped together with a container that contains the composition. Alternatively, the instructional material may be shipped separately from the container with the intention that the instructional material and the composition be used cooperatively by the recipient.

The method of the invention includes a kit comprising a compound identified in the invention and an instructional material that describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques that are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations that become evident as a result of the teaching provided herein.

EXAMPLES

Example 1: Synthesis of 7-amino-2-phenylthieno[3,2-c]pyridin-4(5H)-one (JMS-631-050 (5))

Figure 1:
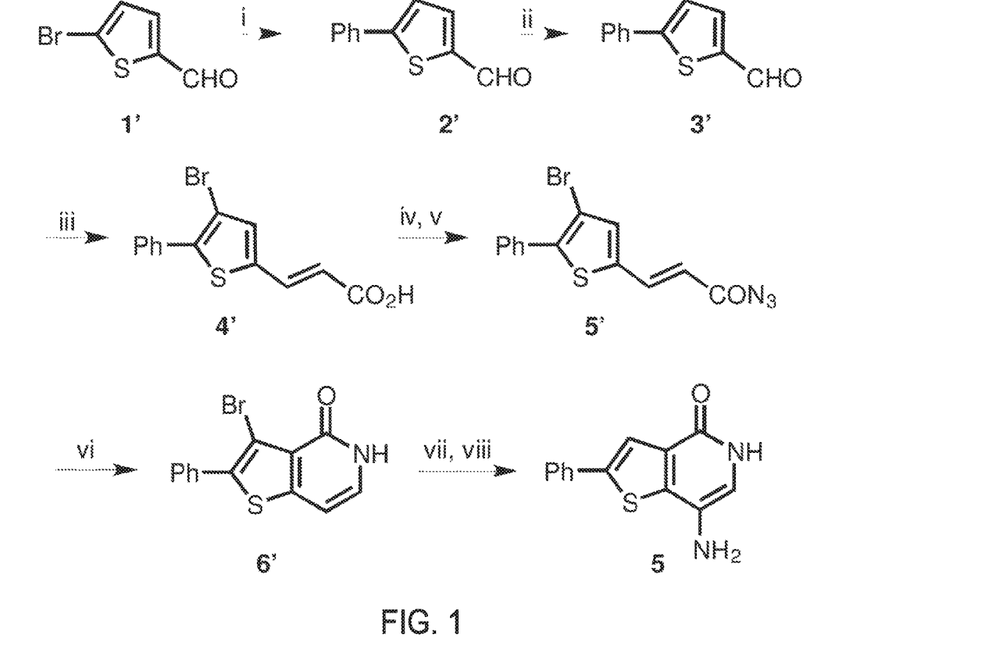
FIG. 1 is a scheme for the synthesis of thienopyridone (5). Reagents and conditions were as follows: (i) Pd(PPh$_3$)$_4$, PhB(OH)$_2$, Na$_2$CO$_3$, dioxane/H$_2$O, μW 90° C., 2 h, 95% (ii) Br$_2$, CHCl$_3$/AcOH, room temperature, 20 h, 98%; (iii) malonic acid, pyridine, piperidine, reflux, 5.5 h, 88%; (iv) SOCl$_2$, DMF, toluene, reflux, 2.5 h; (v) NaN$_3$, toluene/H$_2$O, 0° C. to room temperature, 1.5 h, 44% (2 steps); (vi) Ph$_2$O, μW 250° C., 30 min, 52%; (vii) HNO$_3$, H$_2$SO$_4$, 1 h, 80° C.; (viii) H-cube (1 atm), 10% Pd/C, 50° C., 1 h, 9% (2 steps).

In one synthetic approach to, a Suzuki cross-coupling of phenyl boronic acid with brominated thiophene 1' provided aldehyde 2' in 95% yield 5 (FIG. 1). Regioselective bromination of 2' led to trisubstituted thiophene 3' in high yield. The bromine substituent was envisioned to offer a handle for further functionalizations. Knoevenagel condensation of 3' with malonic acid gave an 88% yield of acid 4' which was subjected to acid chloride formation and substitution with sodium azide to give acyl azide 5' in 44% yield over two steps. Curtius rearrangement and concomitant cyclization required high temperatures and produced thienopyridone 6' in 52% yield. Finally, nitration followed by hydrogenation gave 5 in 9% yield over two steps.

Forming the thienopyridone bicyclic system via a tandem Curtius rearrangement-cyclization is a well-known strategy, but this process requires high temperatures in part to isomerize the trans-double bond to allow the cyclization to take place. In agreement with literature reports, we experienced difficulties with reproducing yields and reaction scale-up was challenging.

Therefore, the following alternative synthetic approach was adopted in part to avoid the alkene isomerization step of the method above.

(a) Primary amine 1 was treated with $CO(OCCl_3)_2$ in a biphasic mixture of $NHCO_3$ (aq) and $CH_2Cl_2$ at 0° C. for 5 h to generate an intermediate isocyanate. Subsequent Friedel-Crafts cyclization was effected by addition of $FeCl_3$ in $CH_2Cl_2$ at 50° C. for 40 minutes to give lactam 2 in 71% yield.

(b) Lactam 2 from step (a) was brominated by treatment with $Br_2$ in acetic acid at room temperature to give intermediate 3 in 75% yield.

(c) Intermediate 3 was subjected to Suzuki cross-coupling with $PhB(OH)_2$, $Pd(PPh_3)_4$ in dioxane/$H_2O$ at 90 90° C. for 24 h, followed by aromatization with DDQ in dioxane at 101° C. over 2 days to give thienopyridone 4 in 48% yield (two steps).

(d) Thienopyridone 4 was nitrated $HNO_3$/acetic acid at room temperature for 15 h, and the intermediate nitrate was hydrogenated in EtOH under $H_2$ (1 atm) with 10% Pd/C (17 mol %) at room temperature for 5 h to give the title compound 5 in 19% yield (two steps).

Example 2: Synthesis of 7-imino-2-phenylthieno[3,2-c]pyridine-4,6(5H,7H)-dione (JMS-631-053)

Compound 5 was subjected to photooxygenation under a variety of conditions as summarized below in Table 1:

TABLE 1

Photooxygenation of 5 to 6.

| Entry | Solvent | Light Source | Conversion Time[a] (isolated yield of 6) |
|---|---|---|---|
| 1 | MeOH[b] | ambient light | >2 d (nd) |
| 2 | HFIP[b] | ambient light | 1 d (trace) |
| 3 | MeOH[b] | 23 W CFL[c] | 18 h (>80%) |
| 4 | MeOH[d] | 23 W CFL[c] | 23 h (85%) |
| 5 | MeOH[e] | 23 W CFL[c] | 2.5 d (77%) |

[a]Monitored by HR LC/MS for disappearance of 5;
[b]On a 7-8 mg scale of 5 at 1-1.1 mg/mL conc.;
[c]Compact fluorescent lamp at a distance of 15 cm;
[d]6.0 mg of 5 in 5.5 mL of MeOH;
[e]32.5 mg of 1 in 30 mL of MeOH;
nd = not determined The reaction under ambient laboratory light generated the novel 7-imino-2-phenylthieno[3,2-c]pyridine-4,6(5H,7H)-dione 6, but the conversion was incomplete with a significant amount of 5 left after 2 days (entry 1). The photooxygenation was also attempted in a halogenated solvent by replacing MeOH with hexafluoroisopropanol (HFIP), but only a trace conversion of 5 to 6 was observed (entry 2). Conversely, placing a 23-W compact fluorescent lamp (CFL) at a distance of 15 cm away from the reaction mixture in a borosilicate or Pyrex flask completed this transformation in 18 h (entry 3), and a yield of 85% was obtained after 23 h (entry 4). Due to its poor solubility in MeOH, 6 started to precipitate out of solution within a few hours. It is worth noting that this transformation was accomplished without the use of any additives, and the product isolation required a simple filtration for purification. Compound 6 was acquired as an amorphous brown powder from MeOH in an average yield of 81% (Table 1, entries 4-5).

Example 3: In Vitro Biochemical Evaluation

The in vitro biochemical evaluation of all compounds was carried out using recombinant human PTP4A3, overexpressed as a His$_6$-tag fusion protein in *E. coli* and purified on a metal affinity column. Assays were performed using 6,8-difluoro-4-methylumbelliferyl phosphate (DiFMUP) as an artificial substrate at 25° C. for 30 min in 40 mM Tris-HCl (pH 7.0), 75 mM NaCl, 2 mM EDTA, and 4 mM DTT buffer. The reaction was carried out in 45 μL total volume per well of a black 384-well plate and initiated upon addition of DiFMUP at a final concentration of 12 μM (3× the K$_m$ of PTP4A3 for DiFMUP, to ensure that the reaction velocity remained constant throughout the assay) to each well containing 1 μg of full-length protein. The fluorescence was measured using a SpectraMax M5 plate reader at 358 nm excitation and 455 nm emission. Fluorescence values were used to calculate the percent inhibition of enzyme activity relative to maximal activity, PTP4A3 in the absence of inhibitor, and maximal inhibition, PTP4A3 in the presence of 2 mM Na$_3$VO$_4$.

Results of the assay are shown in Table 2 below:

TABLE 2

In vitro evaluation of inhibition of PTP4A3 activity.

| Compound | IC$_{50}$ [μM ± S.D.][a] |
|---|---|
| Thienopyridone (5) | 0.132 ± 0.003 |
| JMS-631-053 (6) | 0.018 ± 0.014 |
| JMS-557-038 | >250 |

[a]n = 3.

Consistent with previous reports (S. Daouti, et. al., *Cancer Res.*, 2008, 68, 1162), 5 had an IC$_{50}$ of 132 nM against PTP4A3. The novel imino-pyridinedione 6, in contrast, exhibited a greatly improved IC$_{50}$ of 18 nM, making it the most potent PTP4A3 inhibitor reported to date. Moreover, 6 was about three times more potent against PTP4A3 vs PTP4A1 and PTP4A2, which showed IC$_{50}$ values of 50 and 52 nM, respectively, in our assay. We observed no significant inhibition of the enzymatic activity of another protein tyrosine phosphatase, PTP1B, with concentrations of 6 as high as 80 μM. Further, under the assay conditions (90 min, in the presence or absence of DTT), we did also not detect quantifiable (>5%) spontaneous conversion of 5 to 6.

Example 4: Compound Activity Against Human Ovarian Cancer Cells

Human ovarian cancer cell line drug susceptibility assays were performed in final volumes of 25 μL in a 384-well microtiter format. Human ovarian cancer cells (500) were seeded, compounds or vehicle control were added, and plates were incubated for 44 h. Alamar blue (5 μL) was then added and the cells were incubated for 4 h. Data were captured on a SpectraMax M5 (Ex/Em A$_{560}$/A$_{590}$) and EC$_{50}$ was determined using GraphPad Prism.

Compound BR-1 was used as a positive control, and compound JMS-557-038 was used as a negative control:

BR-1

JMS-557-038

Results of the assay are shown in Table 3 below.

TABLE 3

Compound Activity Against Human Ovarian Cancer Cells

| | | $EC_{50}$ (μM) | | |
|---|---|---|---|---|
| Cell Line | BR-1 | Thienopyridone (5) | JMS-631-053 (6) | JMS-557-038 | Cisplatin |
| SKOV3 | 48.3 ± 9.1 | 28.8 ± 2.2 | 4.3 ± 1.1 | >50 | >100 |
| OVCAR-4 | 48.5 ± 7.9 | 15.5 ± 2.4 | 1.5 ± 0.3 | >50 | 30.3 ± 4.4 |
| A2780CW (Cisplatin sensitive) | 26.4 ± 1.0 | 4.5 ± 0.6 | 0.6 ± 0.2 | >50 | 3.7 ± 1.8 |
| A2780CP20 (Cisplatin resistant) | 17.3 ± 2 | 13.1 ± 06 | 1.1 ± 0.04 | >50 | >100 |

Example 5: Drug Likeness

A computational evaluation was undertaken to determine the drug-likeness of several compounds, as calculated using Osiris Property Explorer. Table 4 below shows the results of the evaluation, identifying compound 6 (JMS-631-053) as an excellent candidate.

TABLE 4

Computational evaluation of drug-likeness

| | BR-1 | Thienopyridone (5) | JMS-631-053 (6) | JMS-557-038 |
|---|---|---|---|---|
| cLog P | 3.94*** | 2.12* | 1.54*** | 2.38*** |
| Solubility | −6.51* | −4.28* | −3.43*** | −4.66** |
| Overall drug-likeness score | −0.16* | 0.79** | 0.87*** | 0.74** |

*** = desirable
** = moderate
* = undesirable

Example 6: Phosphatase Inhibition Assay

The ability of JMS-631-053 (6) to inhibit other phosphatases was assayed by Eurofins Pharma Discovery Services (Dundee, UK) using DiFMUP (6,8-difluoro-4-methylumbelliferyl phosphate) as a substrate and a single concentration of JMS-631-053 (6) measured in duplicate 384 wells. Inhibition of recombinant CDC25B phosphatase (55 ng per 384 well) was also determined using DiFMUP (6,8-difluoro-4-methylumbelliferyl phosphate) as a substrate after a 30 minute incubation. Ex/Em $A_{358}/A_{455}$. Results of the assays are shown below in Table 5.

TABLE 5

Phosphatase Inhibition Assay

| Phosphatase | % inhibition (JMS-631-053 @ 1 μM) mean ± Standard Deviation |
|---|---|
| CD45 | 12.0 ± 2.8 |
| DUSP22 | 9.5 ± 6.4 |
| HePTP | 3.5 ± 3.5 |
| Lambda PP | 28.0 ± 2.8 |
| LMPTP-A | 5.0 ± 4.2 |

TABLE 5-continued

Phosphatase Inhibition Assay

| Phosphatase | % inhibition (JMS-631-053 @ 1 μM) mean ± Standard Deviation |
|---|---|
| LMPTP-B | 1.5 ± 0.7 |
| MKP5 | 13.0 ± 0.0 |
| PP1α | 25 ± 0 |
| PP5 | 4.5 ± 2.1 |
| PTP MEG1 | 0.5 ± 2.1 |
| PTP MEG2 | 12.5 ± 4.9 |
| PTP-1B | 10.0 ± 5.7 |
| PTPN22 | 6.5 ± 2.1 |
| PTPβ | 5.0 ± 4.2 |
| RPTPμ | 20.5 ± 0.7 |
| SHP-1 | 3.5 ± 10.6 |
| SHP-2 | 0.5 ± 9.2 |
| TCPTP | 5.0 ± 2.8 |
| TMDP | 5.0 ± 1.4 |
| VHR | 13.0 ± 11.3 |
| YopH (Yersinia) | 14.0 ± 4.2 |
| CDC25B | 43.8 ± 13.0 |

Example 7: Listing of Thienopyridone (5) Activity Against Phosphatases

For comparative purposes, Table 6 below example lists the activity of thienopyridone (5) against various phosphatases, as reported by B. Hoeger et al. "Biochemical evaluation of virtual screening methods reveals a cell-active inhibitor of the cancer-promoting phosphatases of regenerating liver." Eur. J. Med. Chem. 88 (2014) 89-100.

TABLE 6

Thienopyridone's inhibition profile against phosphatases.

| Phosphatase | $IC_{50}$ (μM) |
|---|---|
| PTP4A3 | 0.457 |
| LARD1 | >100 |
| PTP1B | >100 |

TABLE 6-continued

Thienopyridone's inhibition profile against phosphatases.

| Phosphatase | IC$_{50}$ (µM) |
|---|---|
| PTPaD1 | >100 |
| PTPeD1 | >100 |
| PTPb cat | 67 |
| SHP2 cat | >100 |
| HCP cat | 71 |
| PTPgD1 | >100 |
| YOP(H?) | 61 |
| CD45 | >100 |
| PTP-Tcell | >100 |

Inhibition was determined using DiFMUP as a substrate.

Example 8: Tumor Cell Migration Assay

Cells that were isolated from colorectal tumors of Ptp4a3-wildtype mice were treated with azoxymethane and dextran sodium sulfate (Cramer et al. Stem Cell Res. 13:164, 2014), and were made feeder layer-independent by serially decreasing the feeder layer and increasing the fetal bovine serum concentration. The resulting cells were infected with either a GFP/Cre or a GFP adenovirus. Four days after infection the cells were examined for green fluorescence, PTP4A3 mRNA levels by RT-PCR and protein levels by Western blotting. Green fluorescent cells were isolated by flow cytometry.

Figure 2:
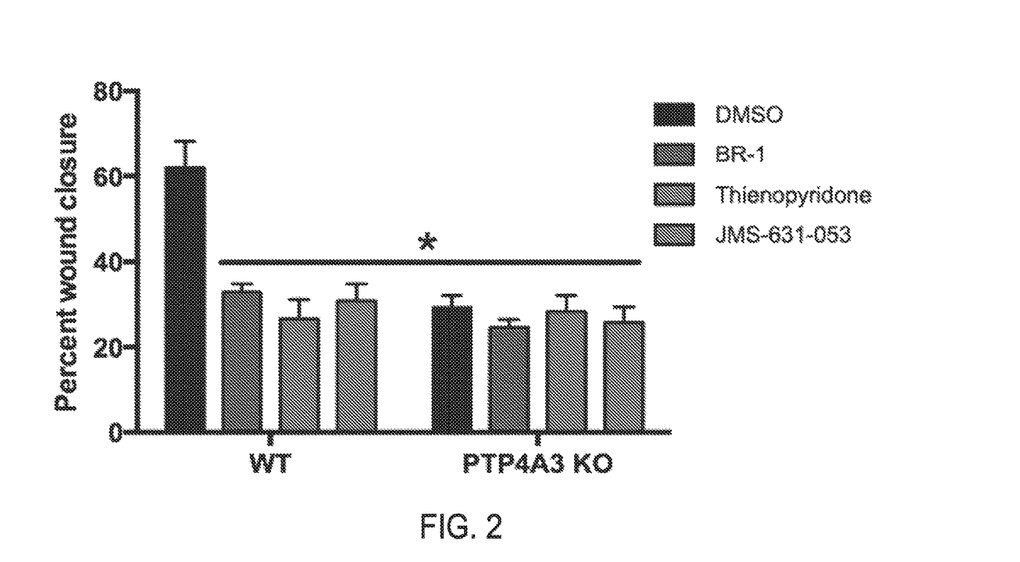
FIG. 2 is a chart showing results from a tumor cell migrations assay of compounds described herein. WT=wild-type; KO=knock-out. N=3±S.E. * p<0.05.

Confluent MsTuWT & MsTuKO cultures were scratched longitudinally with a pipette tip. Cells were exposed to 15 µM BR-1, thienopyridone (5), JMS-631-053 (6), or DMSO vehicle with complete medium and serum for 24 h. Migration was determined by measuring the gap closure between cell fronts using ImageJ. WT=wild-type; KO=knock-out. N=3±S.E. * p<0.05. Results of the assay are shown in FIG. 2.

Example 9: Cell Adhesion Assay

Figure 3:
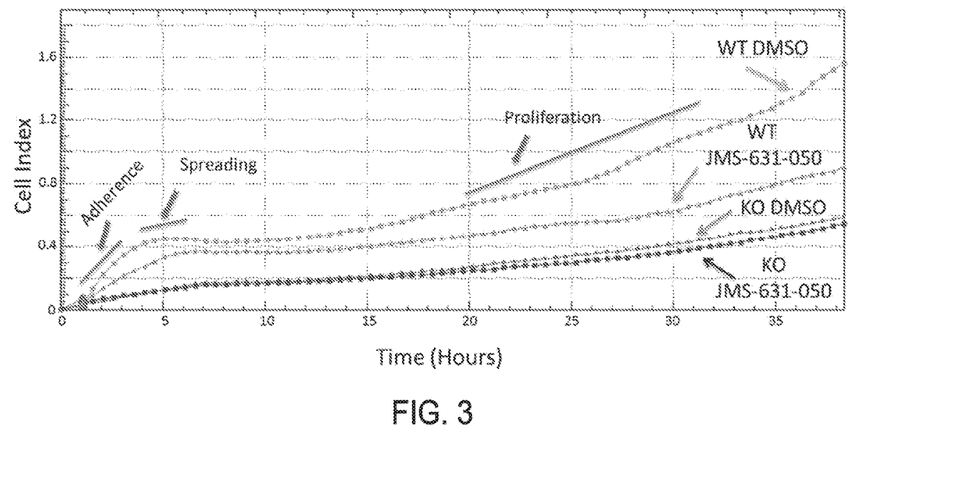
FIG. 3 shows results of cell adhesion assays with thienopyridone (5) (WT=PTP4A3 wild-type; KO=PTP4A3 knock-out).
Figure 4:
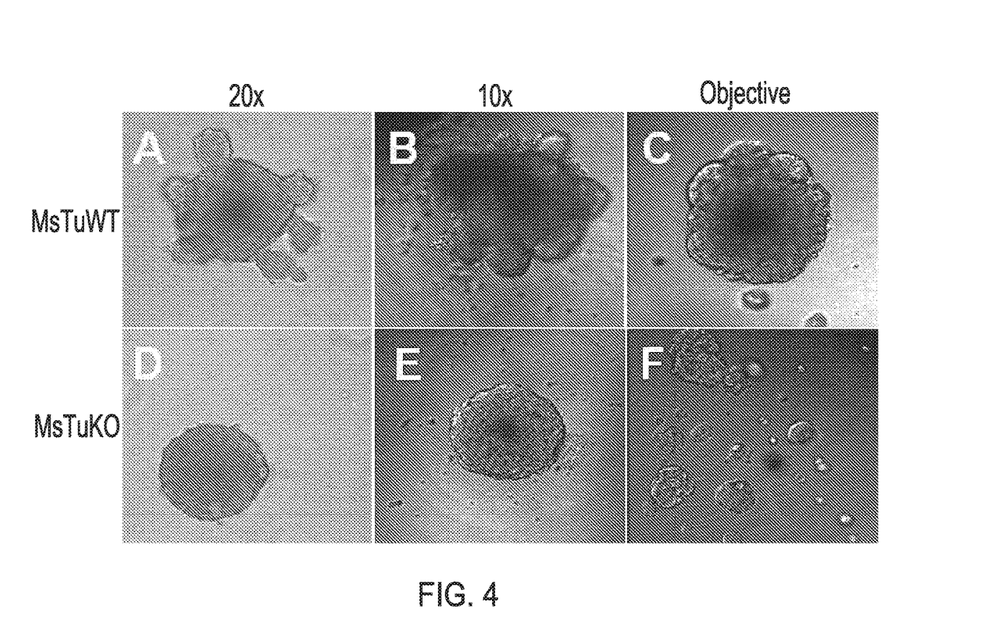

Ptp4a3 wildtype (WT) and null (KO) cells (10,000 per well) were plated into xCELLigence plates, which are high-density gold electrode arrays printed on 96-well sized plates. Cell adhesion and growth of MuTsWT and MuTsKO cells were monitored in real-time with the xCELLigence biosensor, which detects cell attachment, spreading and numbers based on changes in impedance, reported as a unit-less measurement: Cell Index (FIG. 3). These results demonstrate that MsTuKO were less adherent than MsTuWT cells and MsTuWT but not MsTuKO adherence was inhibited by JMS-631-050 (5) (FIG. 4).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

We claim:

1. A compound according to Formula III or a pharmaceutically acceptable salt thereof:

(III)

wherein
R$^4$ is selected from the group consisting of H, —OH, —OC$_{1-4}$ alkyl, —OR$^a$, trifluoroC$_{1-4}$ alkoxy, —SC$_{1-4}$ alkyl, —SR$^a$, —SO$_2$—C$_{1-4}$ alkyl, —SO$_2$R$^a$, —SOC$_{1-4}$ alkyl, —SOR$^a$, —SO$_2$NHR$^b$, —NR$^c$R$^d$, halo, —C$_{1-12}$ alkyl, —C$_{2-6}$ alkenyl, —C$_{2-6}$ alkynyl, —C$_{3-6}$ cycloalkyl, phenyl, benzyl, monocyclic heteroaryl optionally substituted with R$^b$, —C$_{4-7}$ heterocycloalkyl containing one or two of O, S, and N, —OC(O)R$^b$, —OC(O)R$^b$, —P(O)(OR$^b$)$_{1-2}$, —P(S)(OR$^b$)$_{1-2}$, —P(O)(NR$^c$R$^d$)$_{1-2}$, —P(S)(NR$^c$R$^d$)$_{1-2}$, —O(CH$_2$—CH$_2$—O)$_{1-4}$CH$_3$, —CN, —NO$_2$, —C(O)C$_{1-4}$ alkyl, and —C(O)—R$^b$,

R$^a$ is selected from the group consisting of —C$_{3-6}$ cycloalkyl, —C$_{2-6}$ alkenyl, —C$_{2-6}$ alkynyl, phenyl, benzyl, and monocyclic heteroaryl, wherein the phenyl, benzyl, or monocyclic heteroaryl is optionally substituted with R$^b$;

R$^b$ in each instance is independently selected from the group consisting of H, halo, —OH, —COOH, —C$_{1-12}$ alkyl, phenyl, benzyl, and monocyclic heteroaryl, wherein the phenyl, benzyl, or monocyclic heteroaryl is optionally substituted with —C$_{2-6}$ alkenyl, —C$_{2-6}$ alkynyl, trifluoroC$_{1-4}$ alkoxy, —OC$_{1-4}$ alkyl, —O(CH$_2$—CH$_2$—O)$_{1-4}$ CH$_3$, —O-phenyl, —O-benzyl, —NC$_{1-4}$ alkyl, —N-phenyl, and —N-benzyl, or —N-monocyclic heteroaryl;

R$^C$ and R$^d$ are each independently selected from the group consisting of H, —C$_{1-4}$ alkyl, —C(O)—C$_{1-4}$ alkyl, —SO$_2$—R$^a$, —SO$_2$—C$_{1-4}$ alkyl, phenyl, benzyl, and monocyclic heteroaryl, wherein the phenyl, benzyl, or monocyclic heteroaryl is optionally substituted with R$^b$, or R$^C$ and R$^d$ taken together with the nitrogen to which they are attached represent an optionally substituted monocyclic heterocycloalkyl containing one or more of O, S, and N.

2. The compound according to claim 1, wherein the compound is:

or a pharmaceutically acceptable salt thereof.

3. A pharmaceutical composition comprising a therapeutically effective amount of a compound according to Formula III or a pharmaceutically acceptable salt thereof:

(III)

wherein
- $R^4$ is selected from the group consisting of H, —OH, —OC$_{1-4}$ alkyl, —OR$^a$, trifluoroC$_{1-4}$ alkoxy, —SC$_{1-4}$ alkyl, —SR$^a$, —SO$_2$—C$_{1-4}$ alkyl, —SO$_2$R$^a$, —SOC$_{1-4}$ alkyl, —SOR$^a$, —SO$_2$NHR$^b$, —NR$^C$R$^d$, halo, —C$_{1-12}$ alkyl, —C$_{2-6}$ alkenyl, —C$_{2-6}$ alkynyl, —C$_{3-6}$ cycloalkyl, phenyl, benzyl, monocyclic heteroaryl optionally substituted with R$^b$, —C$_{4-7}$ heterocycloalkyl containing one or two of O, S, and N, —OC(O)R$^b$, —OC(O)R$^b$, —P(O)(OR$^b$)$_{1-2}$, —P(S)(OR$^b$)$_{1-2}$, —P(O)(NR$^C$R$^d$)$_{1-2}$, —P(S)(NR$^C$R$^d$)$_{1-2}$, —O(CH$_2$—CH$_2$—O)$_{1-4}$CH$_3$, —CN, —NO$_2$, —C(O)C$_{1-4}$ alkyl, and —C(O)—R$^b$,
- $R^a$ is selected from the group consisting of —C$_{3-6}$ cycloalkyl, —C$_{2-6}$ alkenyl, —C$_{2-6}$ alkynyl, phenyl, benzyl, and monocyclic heteroaryl, wherein the phenyl, benzyl, or monocyclic heteroaryl is optionally substituted with R$^b$;
- $R^b$ in each instance is independently selected from the group consisting of H, halo, —OH, —COOH, —C$_{1-12}$ alkyl, phenyl, benzyl, and monocyclic heteroaryl, wherein the phenyl, benzyl, or monocyclic heteroaryl is optionally substituted with —C$_{2-6}$ alkenyl, —C$_{2-6}$ alkynyl, trifluoroC$_{1-4}$ alkoxy, —OC$_{1-4}$ alkyl, —O(CH$_2$—CH$_2$—O)$_{1-4}$ CH$_3$, —O-phenyl, —O-benzyl, —NC$_{1-4}$ alkyl, —N-phenyl, and —N-benzyl, or —N-monocyclic heteroaryl;
- $R^C$ and $R^d$ are each independently selected from the group consisting of H, —C$_{1-4}$ alkyl, —C(O)—C$_{1-4}$ alkyl, —SO$_2$—R$^a$, —SO$_2$—C$_{1-4}$ alkyl, phenyl, benzyl, and monocyclic heteroaryl, wherein the phenyl, benzyl, or monocyclic heteroaryl is optionally substituted with R$^b$,
- or $R^C$ and $R^d$ taken together with the nitrogen to which they are attached represent an optionally substituted monocyclic heterocycloalkyl containing one or more of O, S, and N, and a pharmaceutically acceptable vehicle.

4. A method for treating a subject suffering from cancer, the method comprising administering to the subject a therapeutically effective amount of a compound according to Formula III or a pharmaceutically acceptable salt thereof:

(III)

wherein
- $R^4$ is selected from the group consisting of H, —OH, —OC$_{1-4}$ alkyl, —OR$^a$, trifluoroC$_{1-4}$ alkoxy, —SC$_{1-4}$ alkyl, —SR$^a$, —SO$_2$—C$_{1-4}$ alkyl, —SO$_2$R$^a$, —SOC$_{1-4}$ alkyl, —SOR$^a$, —SO$_2$NHR$^b$, —NR$^C$R$^d$, halo, —C$_{1-12}$ alkyl, —C$_{2-6}$ alkenyl, —C$_{2-6}$ alkynyl, —C$_{3-6}$ cycloalkyl, phenyl, benzyl, monocyclic heteroaryl optionally substituted with R$^b$, C$_{4-7}$ heterocycloalkyl containing one or two of O, S, and N, —OC(O)R$^b$, —OC(O)R$^b$, —P(O)(OR$^b$)$_{1-2}$, —P(S)(OR$^b$)$_{1-2}$, —P(O)(NR$^C$R$^d$)$_{1-2}$, —P(S)(NR$^C$R$^d$)$_{1-2}$, —O(CH$_2$—CH$_2$—O)$_{1-4}$CH$_3$, —CN, —NO$_2$, —C(O)C$_{1-4}$ alkyl, and —C(O)—R$^b$,
- $R^a$ is selected from the group consisting of —C$_{3-6}$ cycloalkyl, —C$_{2-6}$ alkenyl, —C$_{2-6}$ alkynyl, phenyl, benzyl, and monocyclic heteroaryl, wherein the phenyl, benzyl, or monocyclic heteroaryl is optionally substituted with R$^b$;
- $R^b$ in each instance is independently selected from the group consisting of H, halo, —OH, —COOH, —C$_{1-12}$ alkyl, phenyl, benzyl, and monocyclic heteroaryl, wherein the phenyl, benzyl, or monocyclic heteroaryl is optionally substituted with —C$_{2-6}$ alkenyl, —C$_{2-6}$ alkynyl, trifluoroC$_{1-4}$ alkoxy, —OC$_{1-4}$ alkyl, —O(CH$_2$—CH$_2$—O)$_{1-4}$ CH$_3$, —O-phenyl, —O-benzyl, —NC$_{1-4}$ alkyl, —N-phenyl, and —N-benzyl, or —N-monocyclic heteroaryl;
- $R^C$ and $R^d$ are each independently selected from the group consisting of H, —C$_{1-4}$ alkyl, —C(O)—C$_{1-4}$ alkyl, —SO$_2$—R$^a$, —SO$_2$—C$_{1-4}$ alkyl, phenyl, benzyl, and monocyclic heteroaryl, wherein the phenyl, benzyl, or monocyclic heteroaryl is optionally substituted with R$^b$,
- or $R^C$ and $R^d$ taken together with the nitrogen to which they are attached represent an optionally substituted monocyclic heterocycloalkyl containing one or more of O, S, and N.

5. The method according to claim 4, wherein $R^4$ is selected from the group consisting of H, —OH, —OC$_{1-4}$ alkyl, —OR$^a$, trifluoroC$_{1-4}$ alkoxy, —SC$_{1-4}$ alkyl, —SR$^a$, —SO$_2$—C$_{1-4}$ alkyl, —SO$_2$R$^a$, —SOC$_{1-4}$ alkyl, —SOR$^a$, —SO$_2$NHR$^b$, —NR$^C$R$^d$, halo, and —C$_{1-12}$ alkyl.

6. The method according to claim 5, wherein $R^4$ is H or C$_{1-12}$ alkyl.

7. The method according to claim 6, wherein the compound is:

8. The method according to claim 4, wherein the cancer is selected from the group consisting of colorectal cancer, breast cancer, ovarian cancer, cervical cancer, lung cancer, liver cancer, stomach cancer, and stromal cancer.

9. A method for inhibiting a protein-tyrosine phosphatase in a cell, comprising contacting the cell with a compound according to Formula III or a pharmaceutically acceptable salt thereof:

wherein
- $R^4$ is selected from the group consisting of H, —OH, —$OC_{1-4}$ alkyl, —$OR^a$, trifluoro$C_{1-4}$ alkoxy, —$SC_{1-4}$ alkyl, —$SR^a$, —$SO_2$—$C_{1-4}$ alkyl, —$SO_2R^a$, —$SOC_{1-4}$ alkyl, —$SOR^a$, —$SO_2NHR^b$, —$NR^cR^d$, halo, —$C_{1-12}$ alkyl, —$C_{2-6}$ alkenyl, —$C_{2-6}$ alkynyl, —$C_{3-6}$ cycloalkyl, phenyl, benzyl, monocyclic heteroaryl optionally substituted with $R^b$, —$C_{4-7}$ heterocycloalkyl containing one or two of O, S, and N, —$OC(O)R^b$, —$OC(O)R^b$, —$P(O)(OR^b)_{1-2}$, —$P(S)(OR^b)_{1-2}$, —$P(O)(NR^cR^d)_{1-2}$, —$P(S)(NR^cR^d)_{1-2}$, —$O(CH_2$—$CH_2$—$O)_{1-4}CH_3$, —CN, —$NO_2$, —$C(O)C_{1-4}$ alkyl, and —$C(O)$—$R^b$,
- $R^a$ is selected from the group consisting of —$C_{3-6}$ cycloalkyl, —$C_{2-6}$ alkenyl, —$C_{2-6}$ alkynyl, phenyl, benzyl, and monocyclic heteroaryl, wherein the phenyl, benzyl, or monocyclic heteroaryl is optionally substituted with $R^b$;
- $R^b$ in each instance is independently selected from the group consisting of H, halo, —OH, —COOH, —$C_{1-12}$ alkyl, phenyl, benzyl, and monocyclic heteroaryl, wherein the phenyl, benzyl, or monocyclic heteroaryl is optionally substituted with —$C_{2-6}$ alkenyl, —$C_{2-6}$ alkynyl, trifluoro$C_{1-4}$ alkoxy, —$OC_{1-4}$ alkyl, —$O(CH_2$—$CH_2$—$O)_{1-4}$ $CH_3$, —O-phenyl, —O-benzyl, —$NC_{1-4}$ alkyl, —N-phenyl, and —N-benzyl, or —N-monocyclic heteroaryl;
- $R^c$ and $R^d$ are each independently selected from the group consisting of H, —$C_{1-4}$ alkyl, —C(O)—$C_{1-4}$ alkyl, —$SO_2$—$R^a$, —$SO_2$—$C_{1-4}$ alkyl, phenyl, benzyl, and monocyclic heteroaryl, wherein the phenyl, benzyl, or monocyclic heteroaryl is optionally substituted with $R^b$,
- or $R^c$ and $R^d$ taken together with the nitrogen to which they are attached represent an optionally substituted monocyclic heterocycloalkyl containing one or more of O, S, and N.

10. The method according to claim 9, wherein the protein tyrosine phosphatase is protein tyrosine phosphatase 4A.

11. The method according to claim 10, wherein the protein tyrosine phosphatase 4A is protein tyrosine phosphatase 4A3.

12. A process for preparing a compound of formula 5:

comprising
(a) contacting a compound of formula 1:

with $CO(OCCl_3)_2$, and then subjecting the product to Friedel-Crafts cyclization by contacting the product with $FeCl_3$ to yield a compound of formula 2:

(b) contacting the compound of formula 2 with $Br_2$ in acetic acid to yield a compound of formula 3:

(c) subjecting the compound of formula 3 to Suzuki-cross coupling by contacting the compound with $PhB(OH)_2$ and $Pd(PPh_3)_4$, then aromatizing the cross-coupling product by contacting it with DDQ to yield a compound of formula 4:

and
(d) nitrating the compound of formula 4 by contacting the compound with $HNO_3$/acetic acid, then hydrogenating the product under $H_2$ in the presence of Pd/C to yield the compound of formula 5.

* * * * *